United States Patent [19]

Cummins et al.

[11] 4,452,716
[45] Jun. 5, 1984

[54] MIXED TRIALKYLPHOSPHINE OXIDES AS FUNCTIONAL FLUIDS

[75] Inventors: Richard W. Cummins, Cranbury; Burton M. Baum, Princeton, both of N.J.

[73] Assignee: FMC Corporation, Philadelphia, Pa.

[21] Appl. No.: 451,361

[22] Filed: Dec. 20, 1982

[51] Int. Cl.³ ............................................. C10M 3/38
[52] U.S. Cl. ................................. 252/78.5; 252/49.8; 252/78.1; 568/8; 568/14
[58] Field of Search .................. 252/49.8, 78.1, 78.5; 568/8, 14

[56] References Cited

U.S. PATENT DOCUMENTS

| | | | |
|---|---|---|---|
| 2,149,271 | 3/1939 | Butz | 252/49.9 |
| 2,368,866 | 2/1945 | Nygaard et al. | 44/57 |
| 2,731,458 | 1/1956 | Garwood et al. | 568/8 |
| 2,803,597 | 8/1957 | Stiles et al. | 204/158 |
| 3,104,264 | 9/1963 | Willans | 252/49.8 |
| 3,304,330 | 2/1967 | Yoke et al. | 260/606.5 |
| 3,325,546 | 6/1967 | Hays | 260/606.5 |
| 3,502,730 | 3/1970 | Mason et al. | 22/49.8 |
| 3,732,316 | 5/1973 | Lin | 252/49.8 |
| 3,748,363 | 7/1973 | Maier | 252/49.8 |

OTHER PUBLICATIONS

Pavlenko et al., "Synthesis and Study of the Lubricating Properties of Trialkyl Phosphine Oxides and their Derivatives," Khim. Tekhnol. Topl, Masel (KTPMAG), 68, V13 (5), pp. 28–31.
Journal of Organic Chemistry, 1961—M. M. Rauhut et al., (26, 5138).

Primary Examiner—John E. Kittle
Assistant Examiner—Robert A. Wax
Attorney, Agent, or Firm—Robert D. Jackson; Eugene G. Horsky; Eugene G. Seems

[57] ABSTRACT

Low density hydraulic fluids, in which the base stock is a tri($C_6$–$C_8$–$C_{10}$) alkylphosphine oxide are described.

2 Claims, No Drawings

MIXED TRIALKYLPHOSPHINE OXIDES AS FUNCTIONAL FLUIDS

This invention relates to organophosphorus hydraulic fluids, particularly for use in aircraft.

Modern aircraft are equipped with a number of hydraulically actuated mechanism such as brakes, power steering for taxiing, landing gear, control surfaces, that is, wing flaps, elevator, rudder and the like. In a wide-bodied airliner, the quantity of hydraulic fluid that must be carried can be substantial upwards of about 175 gallons. This amounts to about 200 pounds for the commonly used phosphate ester based hydraulic fluids. A comparable product having a lower specific gravity would be of benefit to the aircraft industry.

It has now been discovered that liquid mixed trialkylphosphine oxides are excellent base stocks in the formulation of low density hydraulic fluids and the provision of such compositions and their use in hydraulic devices and processes constitutes the principal objects and purposes of the invention.

The herein mixed trialkylphosphine oxides contain alkyl radicals each having from 6 to 10 carbon atoms. These compounds, which are known chemical entities, are prepared by phosphinating mixtures of alpha olefins in the presence of a free radical initiator followed by oxidation of the intermediate trialkylphosphine. The reaction can be depicted as follows:

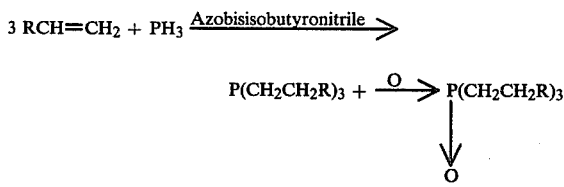

wherein R is mixed alkyl and does not exceed $C_8$. Preferably, $RCH=CH_2$ is an even numbered olefin since these are readily available as byproducts from petroleum refineries. Generally speaking, the reaction sequence is conducted by introducing phosphine into a molar excess of the monoolefin in the presence of the radical initiator under inert conditions at moderately elevated temperatures—about 80° C. to about 120° C. The resulting intermediate phosphine is then oxidized, preferably with hydrogen peroxide, to the corresponding phosphine oxide. Suitable radical initiators include any number of compounds which are photochemically or thermochemically decomposed to form free radicals under the reactive conditions. A preferred radical initiator is azobisisobutyronitrile. Further details and examples of the reaction are set forth in U.S. Pat. No. 2,803,597 to Stiles and J. Org. Chem. 26, 5138 (1961).

The hydraulic fluids of the invention will normally contain very minor amounts, typically about 0.01% to about 5.0% by weight of various additives of the type normally incorporated in formulating hydraulic fluid compositions such as antioxidants, rust inhibitors, corrosion inhibitors, antifoam agents, antiwear agents, cavitation inhibitors, pour point depressants, and other special purpose additives.

Rust and corrosion inhibitors commonly employed include benzothiazole, benzotriazole, triethanolamine, phenothiazine, trialkyl phosphites, N-acrylsarcosines, propyl gallate, succinic acid and alkylsuccinic acids. Additives to inhibit foaming and cavitation include organosilicones, dialkyl carboxylic acid esters such as diethyl succinate or dioctyl sebacate. Antioxidants include dialkylthiodipropionate, for example, dilaurylthiodipropionate, etc., organic amines, for example, diphenylamine, phenylnaphthylamine, hindered phenols, etc.

As previously pointed out, the herein trialkylphosphine oxides are characterized by exceptionally low density and are thus particularly suitable as the base stock in hydraulic fluids for aircraft. Whereas, the common commercial phosphate ester type hydraulic fluids, for example, tributylphosphate and dibutylphenylphosphate have a specific gravity of about at least 1.000, the trialkylphosphine oxides of the invention exhibit an average specific gravity of about 0.878. This translates into substantial weight savings for large commercial airliners such as the 747 which has a hydraulic fluid capacity of about 175 gallons.

The invention is further illustrated by the following example:

Tri($C_6$-$C_8$$C_{10}$) Phosphine Oxide

EXAMPLE 1

To a 1-liter 316 SS stirred autoclave evacuated to 10 mm Hg pressure was added 135.0 g (1.61 moles) of hexene-1, 188.0 g (1.68 moles) off octene-1, 241.0 g (1.72 moles) of decene-1, and 0.4 g of azobisisobutyronitrile. Phosphine (51.0 g, 1.50 moles) was then added and the reaction mixture heated with agitation to 85° C.–90° C. and held at this temperature for a total of 10 hours. A toluene solution of azobisisobutyronitrile, made by dissolving 1.6 of azobisisobutyronitrile in 50 g of toluene, was added in two equal portions after the first and second hours of reaction time.

At the end of the 10 hour reaction period, the reaction mixture was vacuum stripped at 100° C. and 30–50 mm Hg to remove toluene and unreacted olefins and the residue taken up in 600 ml of isopropyl alcohol and oxidized by the dropwise addition of 122 ml of 30% hydrogen peroxide (1.08 moles). The oxidized mixture was vacuum stripped at 30° C. and 5 mm Hg to give 559 g of crude tri($C_6$-$C_8$-$C_{10}$) phosphine oxide corresponding to 96.5% of theory based on phosphine.

The crude product, having an acid number of >4, was dissolved in 300 ml of petroleum ether and stirred for 3 hours with 250 ml of saturated aqueous $Na_2CO_3$ solution and 100 ml of saturated aqueous NaCl solution. After phase separation and vacuum stripping at 30° C. and 5 mm Hg, 378.5 g of liquid product was obtained corresponding to a 65% yield of tri($C_6$-$C_8$-$C_{10}$) phosphine oxide ($C_6$/$C_8$/$C_{10}$=1.0) based on phosphine.

Found: C, 73.93; H, 13.01; P, 8.19. Calculated for $C_{24}H_{51}OP$: C, 74.61; H, 13.21; P, 8.03. Acid number was 0.5. Product was oil-soluble and water-insoluble. Viscosity index was 77. Pour point was +17° F. Specific gravity at 20/20° C. was 0.878. Volume resistivity at 10 volts and 23° C. was $10^6$ ohm-centimeter.

What is claimed is:

1. A hydraulic fluid which comprises as the base stock, 95% to 99.99% by weight of a liquid mixed trialkylphosphine oxide wherein the alkyls are $C_6$ to $C_{10}$, said trialkylphosphine oxide being obtained by phosphinating, in the presence of a free radical initiator, a mixture of the corresponding alpha olefin with phosphine in a molar ratio of 3 to 1 to form a mixed trialkylphosphine followed by oxidation of said mixed trialkylphosphine to the corresponding phosphine oxide and in admixture with the base stock about 0.01% to 5.0% by weight of hydraulic fluid additives.

2. A hydraulic fluid according to claim 1 wherein the mixed trialkylphosphine oxide contains approximately equal molar ratios of alkyls selected from the class consisting essentially of hexyl, octyl and decyl.

* * * * *